United States Patent [19]

Kameswaran

[11] Patent Number: 5,256,796

[45] Date of Patent: Oct. 26, 1993

[54] METHOD FOR THE PREPARATION OF 2-ARYL-5-TRIFLUOROMETHYLPYRROLE COMPOUNDS

[75] Inventor: Venkataraman Kameswaran, Princeton Junction, N.J.

[73] Assignee: American Cyanamid Company, Stamford, Conn.

[21] Appl. No.: 989,271

[22] Filed: Dec. 11, 1992

[51] Int. Cl.$^5$ .............. C07D 207/36; C07D 207/327; C07D 207/34

[52] U.S. Cl. .................... 548/531; 548/557; 548/560; 548/561; 548/562

[58] Field of Search .............. 548/531, 557, 560, 561, 548/562

[56] References Cited

U.S. PATENT DOCUMENTS 5,010,098  4/1991  Brown et al. .................. 514/426
5,128,485  7/1992  Kameswaran .................. 548/561
5,151,536  9/1992  Kameswaran .................. 548/530

OTHER PUBLICATIONS

CA 72(3):12466f Nitro enol, . . . methyl ether, Southwick et al., p. 312, 1970.
CA 101(9):72544g Addition of azlactones, . . . pyrroles, Yebdri et al., p. 627, 1984.
CA 114(23):228662a Carbanion . . . α-methylene-γ-lactams, Patra et al., p. 813, 1991.

*Primary Examiner*—Mary C. Lee
*Assistant Examiner*—Joseph K. McKane
*Attorney, Agent, or Firm*—Michael P. Morris

[57] ABSTRACT

There is provided a method for the preparation of 2-aryl-5-trifluoromethylpyrrole compounds via the reaction of an appropriate haloenamine and alkyl trifluoroacetoacetate. The pyrrole compounds produced are useful as insecticidal, acaricidal and nematocidal agents and as intermediates in the manufacture of said agents.

8 Claims, No Drawings

METHOD FOR THE PREPARATION OF 2-ARYL-5-TRIFLUOROMETHYLPYRROLE COMPOUNDS

BACKGROUND OF THE INVENTION

A wide variety of agronomically harmful insects, acarids and nematodes are efficiently and effectively controlled by 2-aryl-5-trifluoromethylpyrrole compounds.

It is an object of this invention to provide a convenient, direct method for the preparation of arylpyrrole compounds suitable for use in insect, acarid and nematode control. It is another object of this invention to provide a readily utilizable source of important intermediates in the manufacture of further 2-aryl-5-trifluoromethylpyrrole compounds.

SUMMARY OF THE INVENTION

The present invention provides a method for the preparation of a 2-aryl-5-trifluoromethyl pyrrole compound by the reaction of an appropriate haloenamine and alkyl trifluoroacetate in the presence of an acid. In particular, the present invention relates to the preparation of a compound of formula I

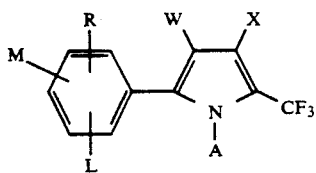

wherein
- A is hydrogen or $C_1$–$C_6$alkyl optionally substituted with phenyl;
- W is CN, $NO_2$ or $SO_2R_2$;
- X is hydrogen or $COOR_1$;
- L is hydrogen or halogen;
- M and R are each independently hydrogen, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, CN, $NO_2$, Cl, Br, F, I, $CF_3$, $R_3CF_2Z$, $R_4CO$ or $NR_5R_6$ and when M and R are on adjacent positions they may be taken together with the carbon atoms to which they are attached to form a ring in which MR represents the structure $-OCH_2O-$, $-OCF_2O-$ or $-CH=CH-CH=CH-$;

- $R_1$ is $C_1$–$C_4$alkyl;
- $R_2$ is $C_1$–$C_6$alkyl, $C_3$–$C_6$cycloalkyl or phenyl;
- $R_3$ is hydrogen, F, $CHF_2$, CHFCl or $CF_3$;
- $R_4$ is $C_1$–$C_4$alkyl, $C_1$–$C_4$alkoxy or $NR_5R_6$;
- $R_5$ is hydrogen or $C_1$–$C_4$alkyl;
- $R_6$ is hydrogen, $C_1$–$C_4$alkyl or $R_7CO$;
- $R_7$ is hydrogen or $C_1$–$C_4$alkyl;
- Z is $S(O)_n$ or oxygen and
- n is an integer of 0, 1 or 2;

which comprises reacting a compound of formula II

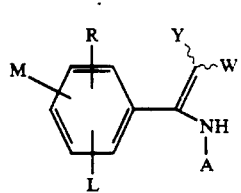

wherein A, W, L, M and R are as described hereinabove and Y is Cl or Br; with about one molar equivalent of $C_1$–$C_4$alkyl trifluoroacetoacetate on the presence of an acid and optionally in the presence of a solvent at an elevated temperature.

Compounds of formula I are effective as insecticidal, acaricidal and nematocidal agents and as important intermediates in the manufacture of said agents.

DETAILED DESCRIPTION OF THE INVENTION

Although there are known methods to synthesize arylpyrrole compounds, commerical-scale manufacturing processes that are economical and environmentally sound are still being sought. The present invention provides a method to obtain useful arylpyrrole compounds and important manufacturing intermediates in a simple single step reaction.

The method for the preparation of a 2-aryl-5-trifluoromethyl pyrrole compound involves the reaction of an appropriate haloenamine and alkyl trifluoroacetate in the presence of an acid. In particular, the present invention relates to the preparation of a compound of formula I

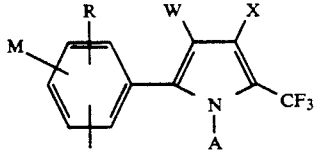

wherein
- A is hydrogen or $C_1$–$C_6$alkyl optionally substituted with phenyl;
- W is CN, $NO_2$ or $SO_2R_2$;
- X is hydrogen or $COOR_1$;
- L is hydrogen or halogen;
- M and R are each independently hydrogen, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, CN, $NO_2$, Cl, Br, F, I, $CF_3$, $R_3CF_2Z$, $R_4CO$ or $NR_5R_6$ and when M and R are on adjacent positions they may be taken together with the carbon atoms to which they are attached to form a ring in which MR represents the structure $-OCH_2O-$, $-OCF_2O-$ or $-CH=CH-CH=CH-$;

- $R_1$ is $C_1$–$C_4$alkyl;
- $R_2$ is $C_1$–$C_6$alkyl, $C_3$–$C_6$cycloalkyl or phenyl;
- $R_3$ is hydrogen, F, $CHF_2$, CHFCl or $CF_3$;
- $R_4$ is $C_1$–$C_4$alkyl, $C_1$–$C_4$alkoxy or $NR_5R_6$;
- $R_5$ is hydrogen or $C_1$–$C_4$alkyl;
- $R_6$ is hydrogen, $C_1$–$C_4$alkyl or $R_7CO$;
- $R_7$ is hydrogen or $C_1$–$C_4$alkyl;
- Z is $S(O)_n$ or oxygen and n is an integer of 0, 1 or 2;
which comprises reacting a compound of formula II

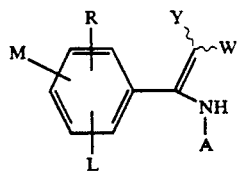
(II)

wherein A, W, L, M and R are as described hereinabove and Y is Cl or Br; with about one molar equivalent of $C_1$-$C_4$alkyl trifluoroacetoacetate in the presence of an acid and optionally in the presence of a solvent at an elevated temperature.

Compounds of formula I, their use as effective insecticidal, acaricidal and nematocidal agents and as important intermediates in the manufacture of said agents are described in U.S. Pat. No. 5,010,098.

In accordance with the method of invention, an appropriately substituted enamine of formula II is reacted with $C_1$-$C_4$alkyl trifluoroacetoacetate in the presence of an acid to give 2-aryl-5-trifluoromethylpyrrole compounds of formula I. The reaction is shown in flow diagram I wherein A, L, M, R, W, X, and Y are as described hereinabove for the arylpyrrole compound of formula I.

Flow Diagram I

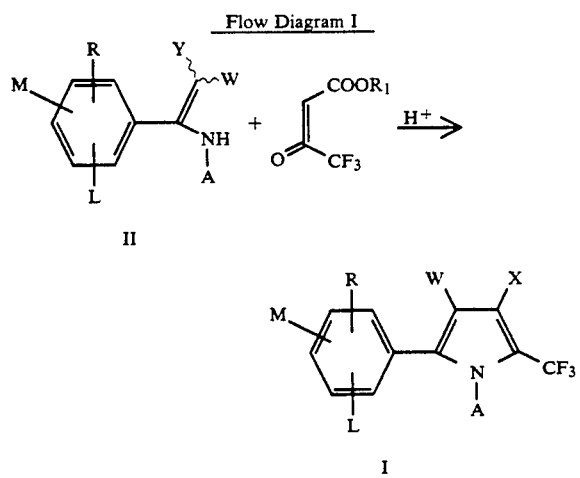

Acids suitable for use in the method of invention are organic acids generally known in the art, in particular carboxylic acids such as acetic acid, propionic acid and the like, preferably acetic acid. A suitable solvent or solvent mixture may optionally be used in conjunction with the organic acid. Such solvents may be selected from organic solvents, such as hydrocarbons, aromatic hydrocarbons, halohydrocarbons, haloaromatic hydrocarbons, and mixtures thereof, which solvent(s) has a boiling point range of about 80° to 250° C.

The method of invention is most efficient at elevated temperatures such as temperatures in the range of about 80° C. to about 250° C. Lower reaction temperatures may significantly increase reaction time and excessively high temperatures may lead to unfavorable side-product formation and decomposition. Preferred temperatures are about 90° to about 180° C.

Compounds of formula II may be prepared by halogenating the appropriate enamine precursor of formula III as shown in flow diagram II.

Flow Diagram II

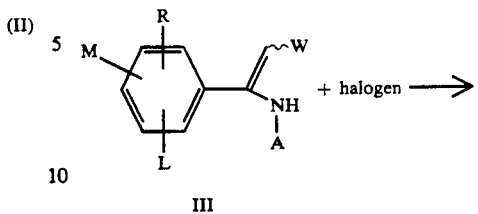

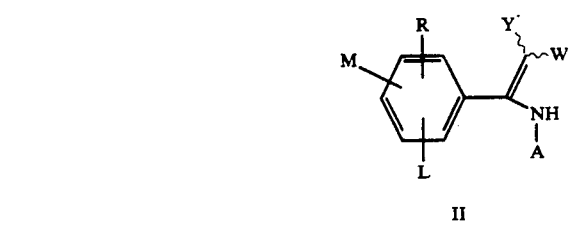

Compounds of formula III and their preparation are described in U.S. Pat. No. 5,128,485.

The 2-aryl-5-trifluoromethylpyrrole compounds of formula I are a source of useful intermediates in the manufacture of important arylpyrrole pesticidal agents. For example, in the instance of a formula I compound wherein X is $COOR_1$, a pesticidal product of formula IV may be obtained directly by a brominative decarboxylation as shown in flow diagram III.

Flow Diagram III

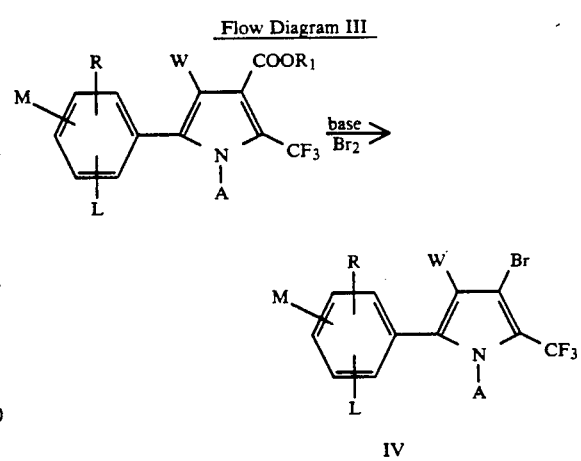

Similarly, a formula I compound wherein X is hydrogen may be readily converted to the desired formula IV product or a 4-halo analogue thereof, by direct halogenation as shown in flow diagram IV.

Flow Diagram IV

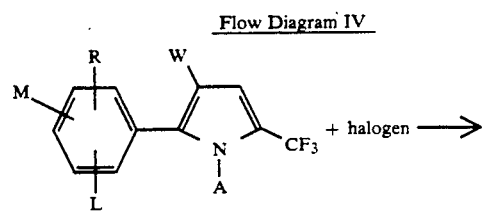

-continued
Flow Diagram IV

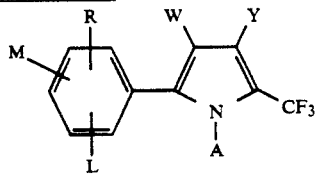

Compounds of formula IV wherein A is hydrogen may be converted to 1-(alkoxymethyl)pyrrole compounds of formula V via reaction with sodium hydride and a dihalomethane reagent in the presence of an alcohol, $R_8OH$. The reaction is shown in flow diagram V.

Flow Diagram V

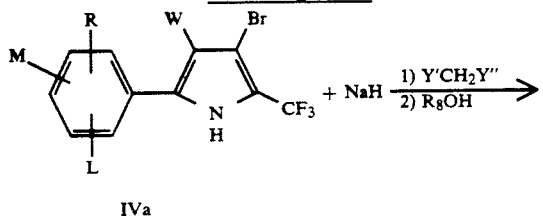

IVa

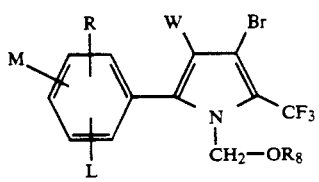

V

In the above flow diagram, Y' and Y" are each independently chlorine, bromine or iodine, $R_8$ is $C_1$-$C_6$alkyl and W, L, M and R are as described hereinabove for the arylpyrrole compound of Formula I.

Compounds of formula V may also be prepared by the procedure described in U.S. Pat. No. 5,151,536. Alternatively, the formula V compounds may be obtained by reacting the appropriate pyrrole intermediate of formula IVa with at least 2 molar equivalents of NaH in an aprotic solvent such as tetrahydrofuran to form the corresponding pyrrole anion, treating the anion with at least 1 molar equivalent of a dihalomethane reagent, optionally at an elevated temperature, to form a reaction mixture, and treating the reaction mixture dropwise with an alcohol, $R_8OH$, so as to maintain a low overall concentration of alcohol in the reaction mixture.

Compounds of formula V, particularly wherein W is CN and $R_8$ is ethyl, more particularly wherein W is CN, $R_8$ is ethyl, L and R are hydrogen and M is chlorine, are highly effective insecticidal, acaricidal and nematicidal agents.

As can readily be seen, a wide variety of pesticidal arylpyrroles may be prepared from the intermediate compounds of formula I by varying the substituents, A, L, M, R and W.

In order to facilitate a further understanding of the present invention, the following examples are set forth. The examples are primarily for the purpose of illustrating certain more specific details and the invention is not to be limited thereby, except as defined in the appended claims. The terms IR and NMR designate infrared and nuclear magnetic resonance, respectively. The term HPLC designates high performance liquid chromatography.

EXAMPLE 1

Preparation of α-Bromo-p-chloro-β-(methylamino)cinnamonitrile, E or Z isomer

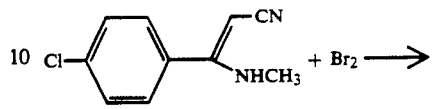

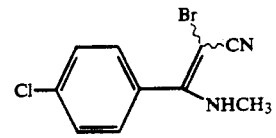

A solution of p-chloro-β-(methylamino)cinnamonitrile (19.3 g, 0.1 mol) in carbon tetrachloride at 70° C. is treated dropwise with a solution of bromine (16.8 g, 0.105 mol) in carbon tetrachloride over a 30-40 minute period (tetrahydrofuran is added as needed during the bromine addition to aid dissolution of the reaction mixture). The reaction mixture is stirred for 30 minutes at 70° C., cooled to room temperature and concentrated to give a yellow crystalline precipitate. The mixture is filtered, the filter cake is washed with carbon tetrachloride and dried to give the title product as a yellow solid, 18.8 g (69% yield), mp 178.0°-178.5° C., identified by IR, NMR and mass spectral analyses.

EXAMPLE 2

Preparation of
2-(p-chlorophenyl)-1-methyl-5-(trifluoromethyl)pyrrole-3-carbonitrile (I) and
4-carbethoxy-2-(p-chlorophenyl)-1-methyl-5-(trifluoromethyl)pyrrole-3-carbonitrile(II)

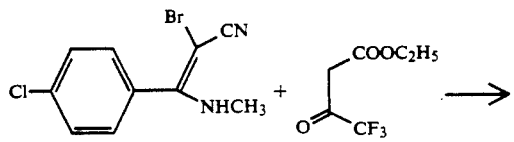

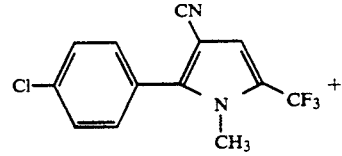

I

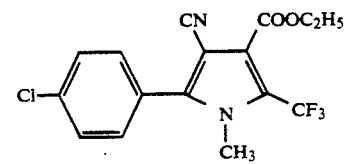

II

A stirred mixture of 2-bromo-p-chloro-β-(methylamino)cinnamonitrile (10.0 g, 0.0368 mol) and ethyl trifluoroacetoacetate (10.17 g, 0.0552 mol) in acetic acid is heated at 116°-118° C. for 7 hours, cooled to room temperature, diluted with water and extracted with ethyl acetate. The extracts are combined, washed with water, dried over Na$_2$SO$_4$ and concentrated in vacuo to give a gum residue. The residue is flash chromatographed using silica gel and 15:1 ethyl acetate:heptane as eluent to give the title product (I) as a white solid, 2.7 g, mp 127°–129° C. identified by $^1$HNMR and $^{19}$FNMR spectral analyses and the other title product (II) as orange crystals, 1.65 g., mp 129°–131° C., identified by $^1$HNMR and $^{19}$FNMR spectral analyses.

EXAMPLE 3

Preparation of
4-bromo-2-(p-chlorophenyl)-5-(trifluoromethyl)pyrrole-3-carbonitrile

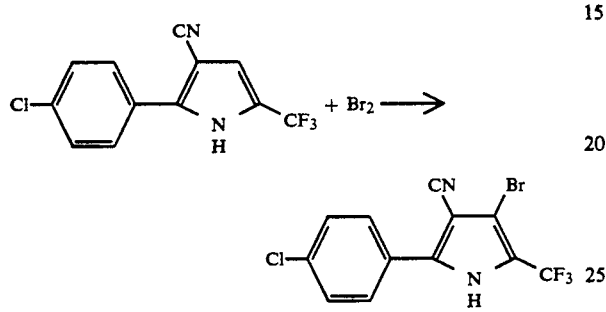

A solution of 2-(p-chlorophenyl)-5-(fluoromethyl)-pyrrole-3-carbontrile (1 equivalent) in carbon tetrachloride is treated with bromine (1.8 equivalents), stirred at ambient temperatures until reaction is complete and concentrated in vacuo to give the title product in quantitative yield, identified by IR, NMR and mass spectral analyses.

EXAMPLE 4

Preparation of
4-bromo-2-(p-chlorophenyl)-1-(ethoxymethyl)-5-(trifluoromethyl)pyrrole-3-carbonitrile

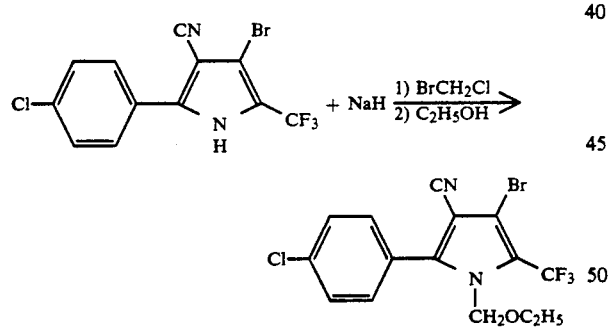

A stirred mixture of sodium hydride (26.5 g, 1.105 mol) in tetrahydrofuran, under nitrogen, is treated slowly with a solution of 4-bromo-2-(p-chlorophenyl)-5-(trifluoromethyl)pyrrole-3-carbonitrile (1.00 g, 0.273 mol) in tetrahydrofuran at ≦60° C. When the addition is complete, the reaction mixture is treated with bromochloromethane (93.0 g, 0.718 mol), heated to 63°–65° C., treated dropwise with absolute ethanol (39.5 g, 0.859 mol) over a 5.5 hour period, stirred at 63°–65° C. for another 3 hours and concentrated in vacuo. The concentrate is dispersed in a mixture of water and methylene chloride. The aqueous phase is separated and washed with methylene chloride. The organic phases are combined and concentrated. The concentrate is dispersed in hexane, cooled to 5°–10° C. and filtered. The filtercake is washed with heptane and dried to give the title product as a white solid, 111.6 g, (91.3% yield) and 91.2% purity by HPLC analysis.

I claim:
1. A method for the preparation of a compound of formula I

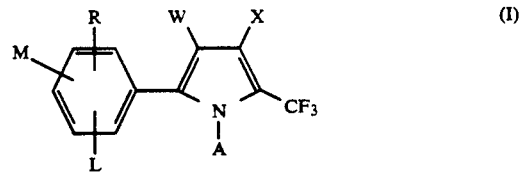

wherein
A is hydrogen or C$_1$-C$_6$alkyl optionally substituted with phenyl;
W is CN, NO$_2$ or SO$_2$R$_2$;
X is hydrogen or COOR$_1$;
L is hydrogen or halogen;
M and R are each independently hydrogen, C$_1$-C$_4$alkyl, C$_1$-C$_4$alkoxy, C$_1$-C$_4$alkylthio, C$_1$-C$_4$alkylsulfinyl, C$_1$-C$_4$alkylsulfonyl, CN, NO$_2$, Cl, Br, F, I, CF$_3$, R$_3$CF$_2$Z, R$_4$CO or NR$_5$R$_6$ and when M and R are on adjacent positions they may be taken together with the carbon atoms to which they are attached to form a ring in which MR represents the structure —OCH$_2$O—, —OCF$_2$O— or
—CH=CH—CH=CH—;

R$_1$ is C$_1$-C$_4$alkyl;
R$_2$ is C$_1$-C$_6$alkyl, C$_3$-C$_6$cycloalkyl or phenyl;
R$_3$ is hydrogen, F, CHF$_2$, CHFCl or CF$_3$;
R$_4$ is C$_1$-C$_4$alkyl, C$_1$-C$_4$alkoxy or NR$_5$R$_6$;
R$_5$ is hydrogen or C$_1$-C$_4$alkyl;
R$_6$ is hydrogen, C$_1$-C$_4$alkyl or R$_7$CO;
R$_7$ is hydrogen or C$_1$-C$_4$alkyl;
Z is S(O)$_n$ or oxygen and
n is an integer of 0, 1 or 2;
which comprises reacting a compound of formula II

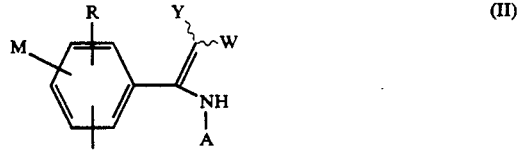

wherein A, W, L, M and R are as described hereinabove and Y is Cl or Br with about one molar equivalent of C$_1$-C$_4$alkyl trifluoroacetoacetate in the presence of an acid and optionally in the presence of a solvent at an elevated temperature.

2. The method according to claim 1 wherein the elevated temperature is about 80° to about 250° C.

3. The method according to claim 2 wherein the acid is acetic acid.

4. The method according to claim 3 wherein the temperature is about 90° to 180° C.

5. The method according to claim 3 wherein W is CN.

6. The method according to claim 5 wherein A is hydrogen or C$_1$-C$_6$ alkyl, and L, M and R are each independently hydrogen or halogen.

7. The method according to claim 5 wherein L is hydrogen and M and R are each independently hydrogen, halogen or CF$_3$.

8. The method according to claim 6 wherein L and R are hydrogen and M is halogen.

* * * * *